(12) United States Patent
Hubbell et al.

(10) Patent No.: US 6,263,726 B1
(45) Date of Patent: Jul. 24, 2001

(54) SIDEWALL TENSIOMETER AND METHOD OF DETERMINING SOIL MOISTURE POTENTIAL IN BELOW-GRADE EARTHEN SOIL

(75) Inventors: Joel M. Hubbell; James B. Sisson, both of Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 08/884,480

(22) Filed: Jun. 27, 1997

Related U.S. Application Data

(62) Division of application No. 08/376,165, filed on Jan. 19, 1995, now Pat. No. 5,644,947.

(51) Int. Cl.[7] ............................. G01N 25/56; G01N 5/02; E21B 49/00
(52) U.S. Cl. ..................... 73/73; 73/152.05; 73/152.06; 73/152.17; 73/152.41
(58) Field of Search ..................... 73/73, 152.05, 73/152.06, 152.17, 152.41, 19.09

(56) References Cited

U.S. PATENT DOCUMENTS

| | | | |
|---|---|---|---|
| 2,878,671 | 3/1959 | Prosser et al. | 73/73 |
| 3,043,133 | 7/1962 | Richards | 73/73 |
| 3,049,914 | 8/1962 | Richards | 73/73 |
| 3,871,211 | 3/1975 | Tal | 73/73 |
| 3,898,872 | 8/1975 | Skaling et al. | 73/73 |
| 4,068,525 | 1/1978 | Skaling | 73/73 |
| 4,520,657 | 6/1985 | Marthaler | 73/73 |

FOREIGN PATENT DOCUMENTS

| | | | |
|---|---|---|---|
| 1174635 | 12/1969 | (GB) | 73/73 |
| 1454674 | 11/1996 | (GB) | 73/73 |

OTHER PUBLICATIONS

James, M. L. et al., *Applied Numerical Methods for Digital Computation*, (3rd), Harper & Row, NY, pp. 86–93.

*Primary Examiner*—Hezron Williams
*Assistant Examiner*—Dennis Loo
(74) *Attorney, Agent, or Firm*—Alan D. Kirsch

(57) ABSTRACT

A sidewall tensiometer to in situ determine below-grade soil moisture potential of earthen soil includes, a) a body adapted for insertion into an opening in earthen soil below grade, the body having lateral sidewalls; b) a laterally oriented porous material provided relative to the body lateral sidewalls, the laterally oriented porous material at least in part defining a fluid chamber within the body; c) a pressure a sensor in fluid communication with the fluid chamber; and d) sidewall engaging means for engaging a portion of a sidewall of an earth opening to laterally urge the porous material into hydraulic communication with earthen soil of another portion of the opening sidewall. Methods of taking tensiometric measurements are also disclosed.

19 Claims, 7 Drawing Sheets

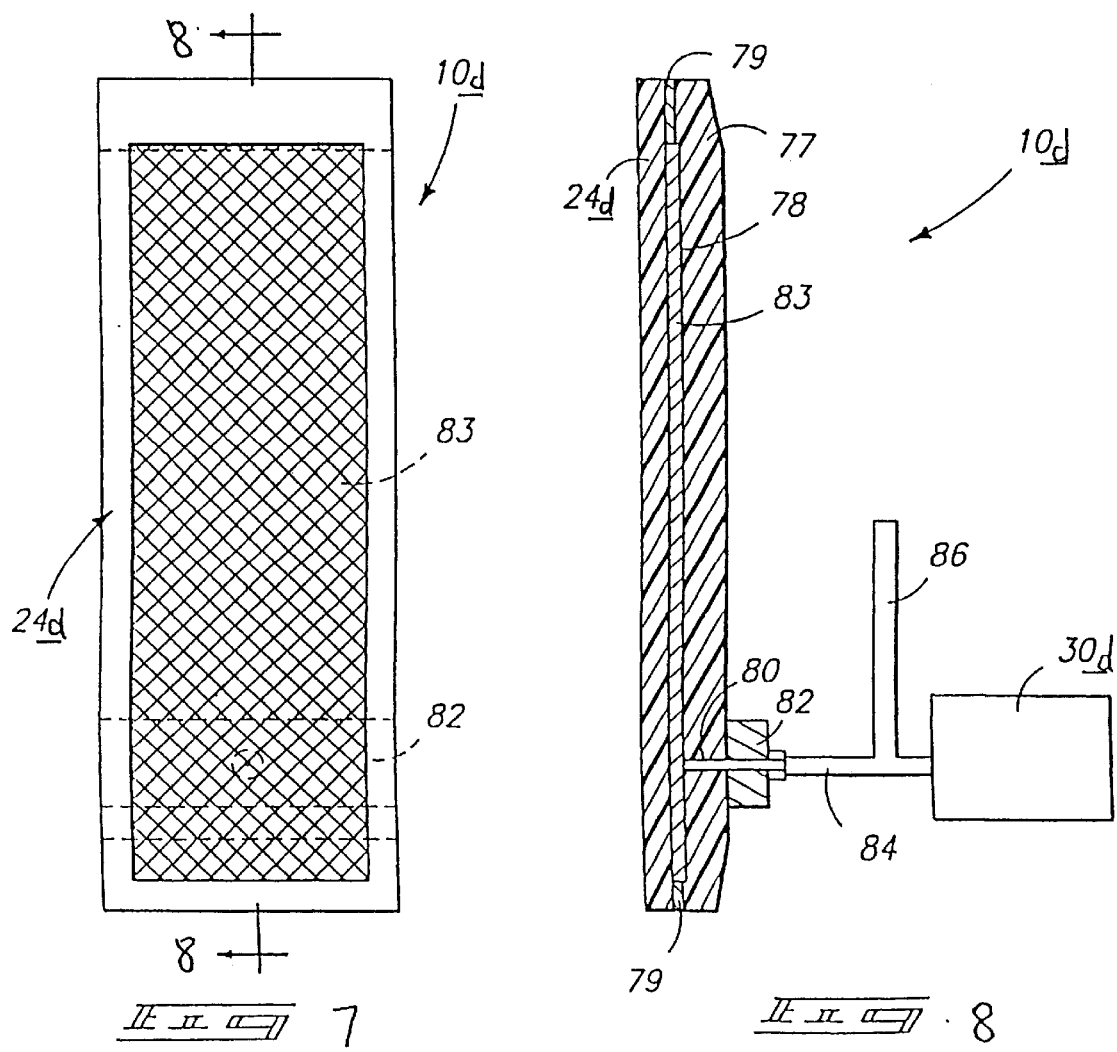

though the porous tip is lengthened. The pressure exerted by the column of water increases the pressure in the porous tip, which in turn increases the apparent soil moisture tension recorded by the above-surface pressure measuring device.

SIDEWALL TENSIOMETER AND METHOD OF DETERMINING SOIL MOISTURE POTENTIAL IN BELOW-GRADE EARTHEN SOIL

This application is a division of application Ser. No. 08/376,165, filed Jan. 19, 1995 now U.S. Pat. No. 5,644,947. +gi

CONTRACTUAL ORIGIN OF THE INVENTION

The United States Government has rights in this invention disclosed under contract number DE-AC07-76ID01570 between the U.S. Department of Energy and EG&G Idaho, Inc., now contract number DE-AC07-94ID13223 with Lockheed Idaho Technologies Company.

TECHNICAL FIELD

This invention relates to tensiometers and to techniques for measuring soil moisture potential using tensiometers.

BACKGROUND OF THE INVENTION

If moisture potential of soil can be accurately monitored, irrigation can be controlled to optimize the rate of plant growth. One type of instrument for measuring soil moisture potential is a tensiometer. A conventional tensiometer comprises a sealed tube defining a chamber which is normally completely filled with water, a hollow porous tip on one end of the tube, and a vacuum gauge connected to the water chamber. The porous tip is inserted in the soil, and establishes liquid contact between the water in the tube and moisture in the soil surrounding the tip. Relatively dry soil tends to pull water from the tube through the porous tip. However since the tube is sealed, only a minute amount of water is actually withdrawn. Accordingly, the water in the tube is placed under tension by the pulling effect of the dry soil, thus creating a measurable subatmospheric pressure in the tube. Higher moisture contents in the soil produce correspondingly less vacuum in the tube, and completely saturated soil registers substantially zero vacuum or atmospheric pressure.

Typical tensiometer constructions provide a tube or column of water which extends from the porous tip to above grade. It will be apparent that the deeper the porous tip is buried, the longer the column of liquid above it will become.

Air presence in the water reservoir during tensiometric measurement is undesirable. Air can enter the reservoir by diffusing through the porous tip. More commonly, dissolved air present in the water that enters the vessel comes out of solution in the reduced pressure environment of the tensiometer. Eventually, the entire tensiometer would become filled with air. This air will increase the time required to reach pressure equilibrium because large volumes of water must move through the porous tip to effect the mass transfer of air through the tip. Thus in order to obtain accurate readings, the water and air are desirably purged periodically from the tensiometer reservoir and replaced with degassed water.

To facilitate purging of air from the tensiometer reservoir, a conventional tensiometer is typically provided with a column of water connecting a surface located pressure measuring device to the soil-embedded porous tip. However, there is a physical limit to the length of a column of water which can be supported by atmospheric pressure (about 1000 cm at sea level), and the useful measurement range of the tensiometer is reduced as the column of water above the porous tip is lengthened. The pressure exerted by the column of water increases the pressure in the porous tip, which in turn increases the apparent soil moisture tension recorded by the above-surface pressure measuring device.

BRIEF DESCRIPTION OF THE DRAWINGS

Preferred embodiments of the invention are described below with reference to the following accompanying drawings.

FIG. 7 is a diagrammatic side elevational view of another alternate embodiment sidewall tensiometer apparatus in accordance with the invention.

FIG. 8 is a side sectional view the FIG. 6 tensiometer apparatus.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In accordance with one aspect of the invention, a sidewall tensiometer to in situ determine below-grade soil moisture potential of earthen soil comprises:

a body adapted for insertion into an opening in earthen soil below grade, the body having lateral sidewalls;

a laterally oriented porous material provided relative to the body lateral sidewalls, the laterally oriented porous material at least in part defining a fluid chamber within the body;

a pressure sensor in fluid communication with the fluid chamber; and sidewall engaging means for engaging a portion of a sidewall of an earth opening to laterally urge the porous material into hydraulic communication with earthen soil of another portion of the opening sidewall.

In accordance with another aspect of the invention, a method of monitoring soil moisture potential in below-grade earthen soil comprises the following steps:

inserting a tensiometer into an earthen opening below grade in earthen soil; the tensiometer having a porous material, a fluid chamber in fluid communication with the porous material, and a degassed liquid within the fluid chamber laterally urging the porous material against a sidewall of the earthen opening to effectively establish hydraulic communication between the fluid chamber and the earthen material;

permitting the degassed liquid to permeate the porous material to cause a change in pressure in the fluid chamber; and determining the change in pressure within the chamber.

Figure 1:
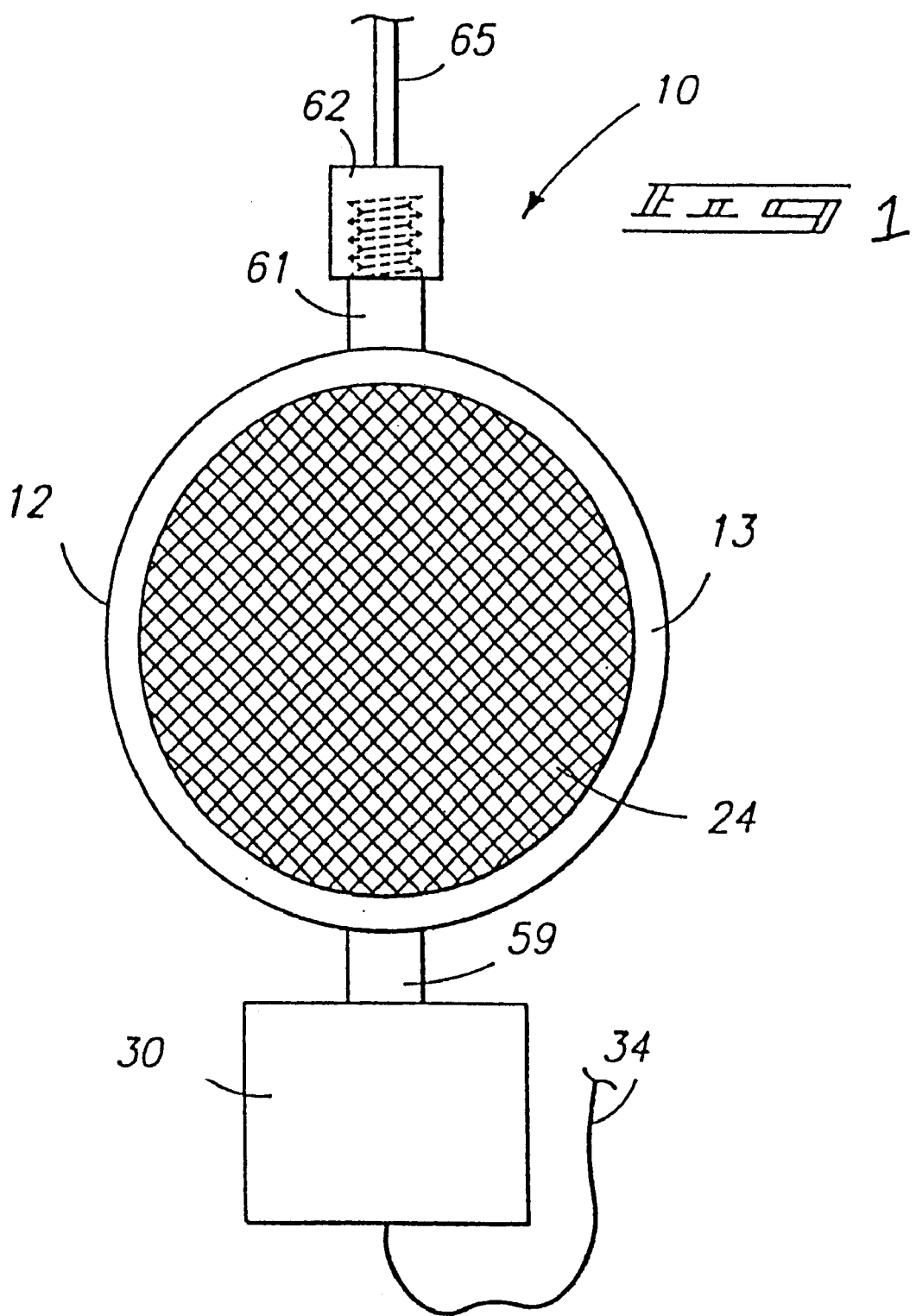
FIG. 1 is a diagrammatic side elevational view of a sidewall tensiometer in accordance with the invention.
Figure 2:
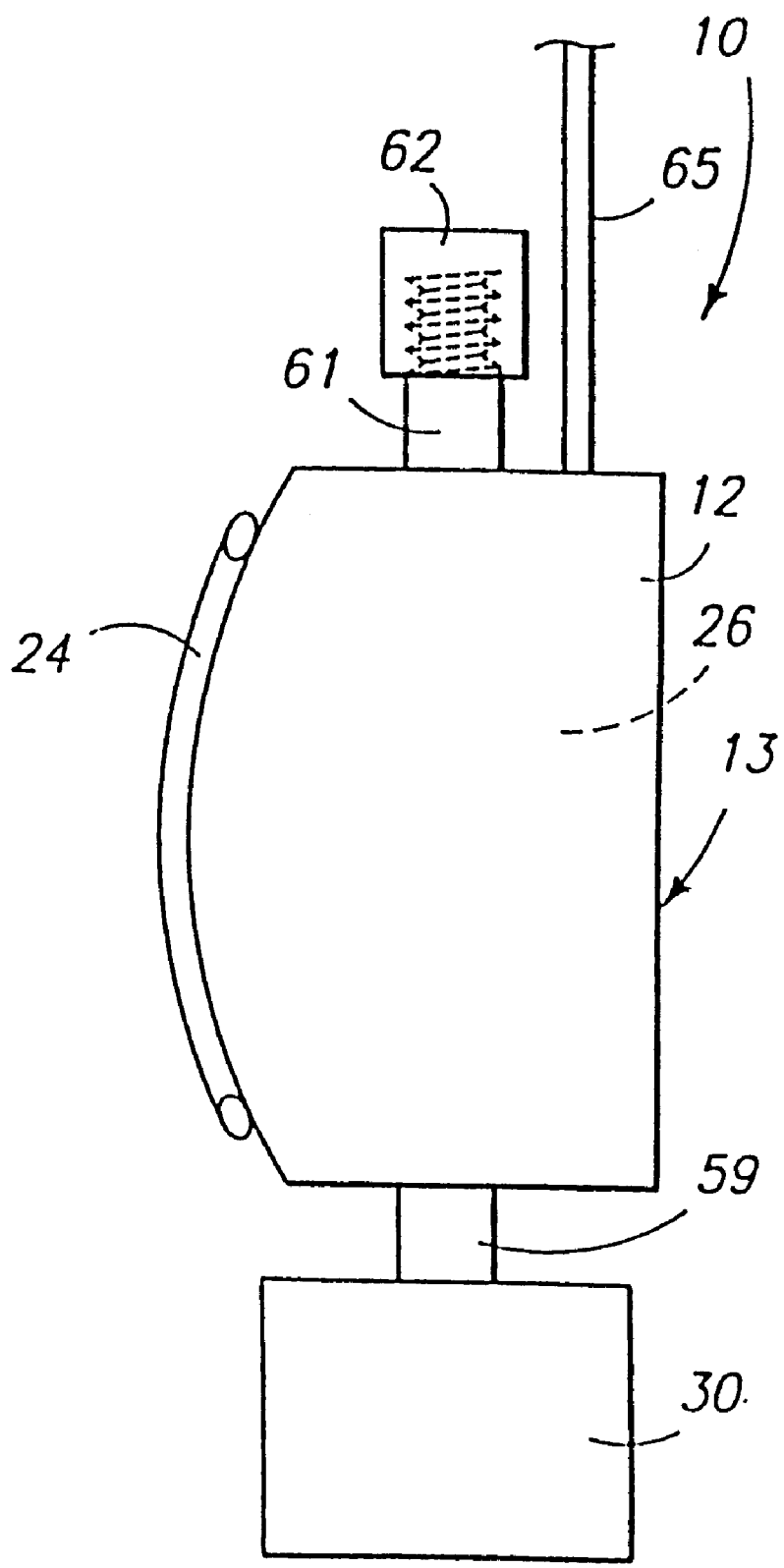
FIG. 2 is a side elevational view corresponding to that of FIG. 1, but for a 90° rotation of the tensiometer.

The sidewall tensiometer and method to in situ determine below-grade soil moisture potential is described with reference to FIGS. 1 and 2. Tensiometer apparatus 10 includes a body 12 which is adapted for insertion into a bore in earthen soil below grade. Body 12 is elongated and has surrounding lateral sidewalls 13. Body 12 is substantially hollow defining an internal fluid chamber 26. An arcuate or curved laterally-oriented, porous material 24 is provided relative to one of body lateral sidewalls 13, and in part defines a boundary of fluid chamber 26 within body 12. A pressure transducer 30 is provided externally of housing 12, and communicates with chamber 26 via a conduit 59. Accordingly in the illustrated embodiment, pressure transducer 30 is mounted externally of housing or body 12. An example transducer is Model ST2P15G1, having a range of from +15 to −15 psig, sold by SenSym of Milpitas, Calif. It could of course also be directly connected to sidewalls 13, or retained internally relative to housing 26. A fill tube 61 extends outwardly of housing 12, and communicates with fluid chamber 26. A sealing cap 62 is provided to seal fluid chamber 26. An electric lead 34 would extend from transducer 30 to the surface. Component 65 diagrammatically illustrates either a flexible line or a rigid rod for utilization in raising or lowering housing 12 relative to a borehole in which the apparatus will be utilized for tensiometric measurements. Alternately, tensiometer apparatus 10 can be raised and lowered using the electrical leads.

To utilize such a device, fluid chamber 26 would be filled with a degassed liquid via fill tube 61. Thereafter, body 12 would be inserted into a bore or trench below grade in earthen soil. Porous member 24 would be laterally urged against a sidewall of the earthen bore to effectively establish hydraulic communication between fluid chamber 26 and earthen material. Degassed liquid would permeate the porous material to cause a change in pressure in fluid chamber 26, which would be monitored by pressure transducer 30. Such a construction method provides an advantage of obtaining tensiometric measurements via sidewall bore access as opposed to hydraulic access within the bore at the base.

Figure 3:
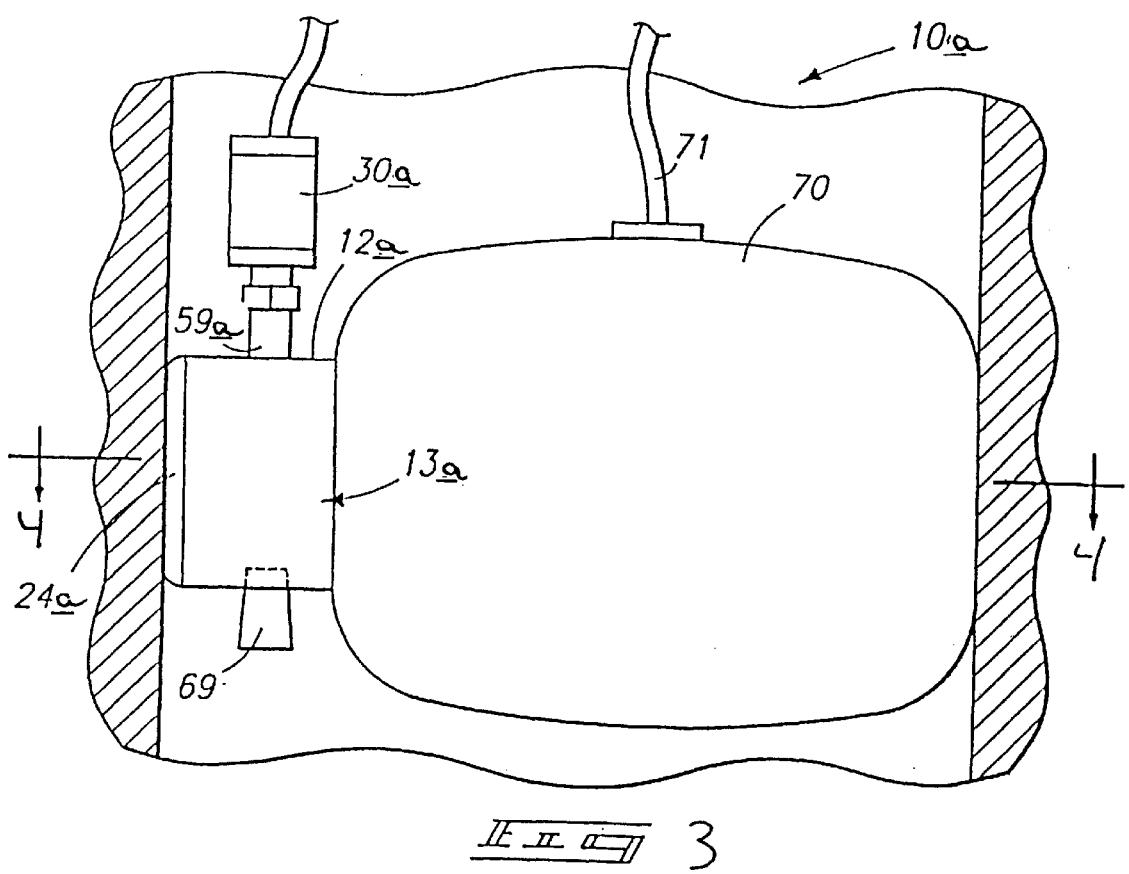
FIG. 3 is a longitudinal sectional view of an alternate embodiment of a sidewall tensiometer device in accordance with the invention as positioned within a borehole for tensiometric measurement.
Figure 4:
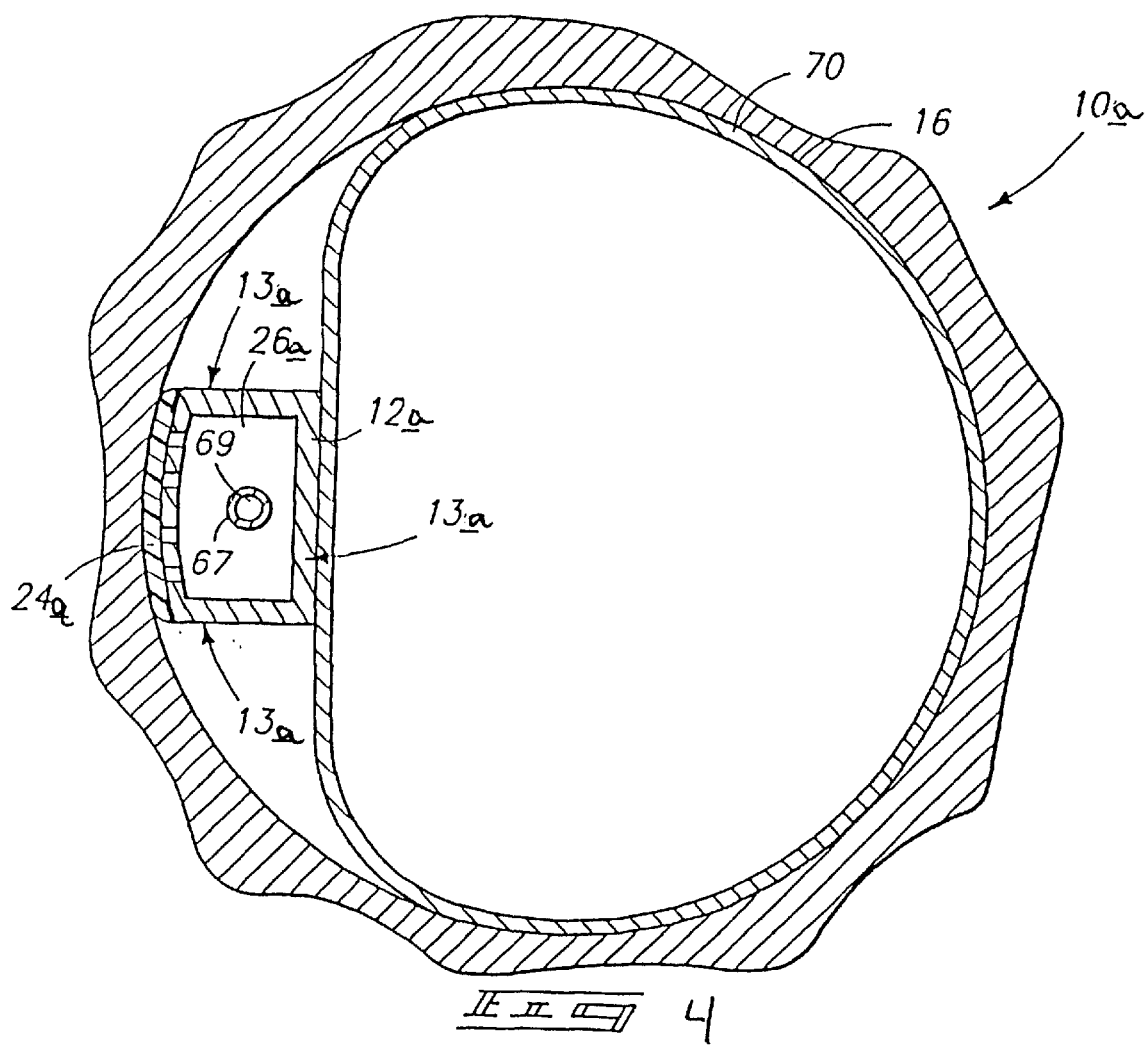
FIG. 4 is a sectional view taken through line 4—4 of FIG. 3.

FIGS. 3 and 4 illustrate a reduction-to-practice tensiometer apparatus 10a in accordance with an aspect of the invention. Like numerals form FIGS. 1 and 2 are utilized with distinctions and construction being indicated by different numerals or a suffix "a". Body 12a is configured with a bottom opening 67 (FIG. 4) which is sealable by means of a rubber stopper 69. Such opening is utilizable to fill fluid chamber 26a with degassed fluid. Porous material 24a in one of body sidewalls 13a preferably has an arcuate periphery, as shown, corresponding in male size and shape to a female arcuate periphery size and shape of the size of bore 16 for which the apparatus is primarily adapted.

An inflatable bladder 70 is provided laterally of porous material 24a against one of lateral sidewalls 13a of housing 12a. Such is preferably adhered by an adhesive or other means to the outer portion of sidewall 13a. An inflation/deflation hose 71 extends outwardly of bladder 70 to an above-grade location.

When positioning apparatus 10a within bore 16, bladder 70 would be initially deflated and the apparatus then lowered to a desired depth within the soil. Thereafter, bladder 70 would be inflated with a fluid (either liquid or gas, or a combination thereof). Such causes the bladder to engage a portion of a sidewall of bore 16 to laterally urge porous material 26a into hydraulic communication with earthen soil of another portion of the bore sidewall, as shown. Tensiometric measurements are then determined after equilibrium is reached, as described above.

Figure 5:
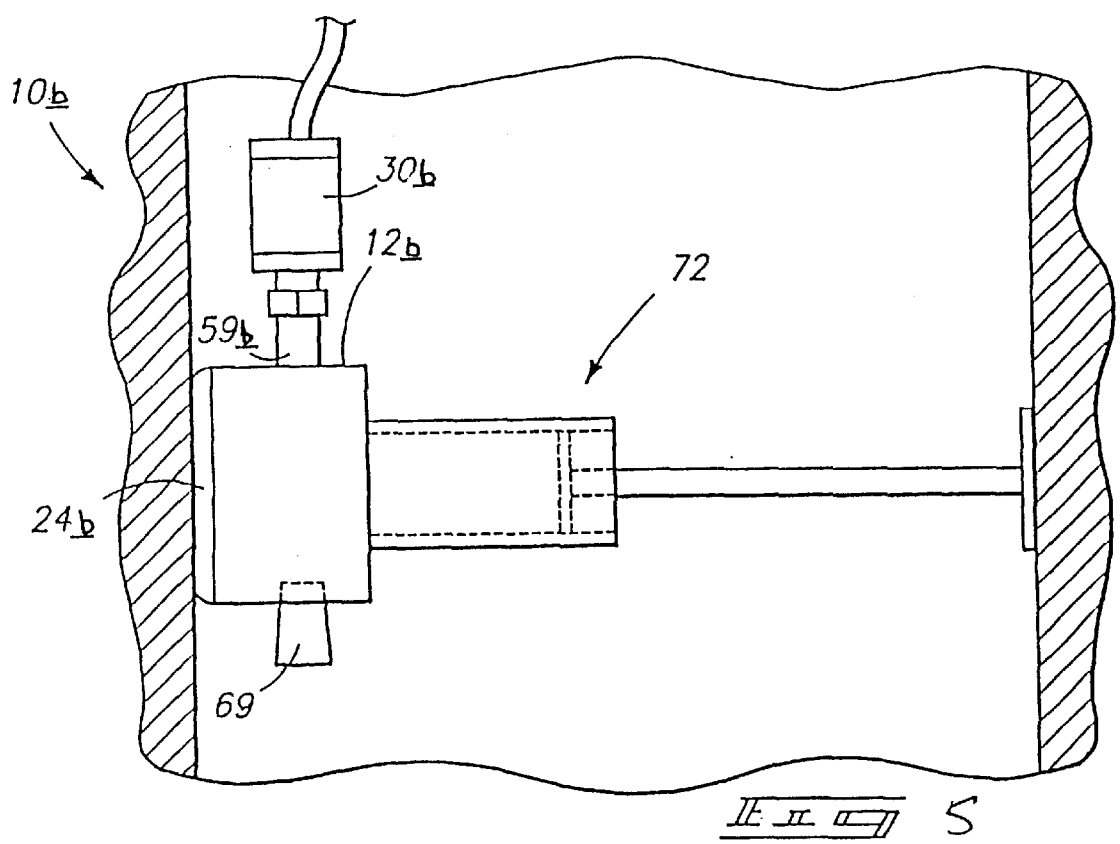
FIG. 5 is a longitudinal sectional view of an alternate embodiment sidewall tensiometer apparatus in accordance with the invention.

Alternate mechanisms might also be utilized for urging porous material 24a against the sidewall of a bore. FIG. 5, by way of example only, illustrates one such alternate construction 10b. Such illustrates in diagrammatic form a piston and cylinder assembly 72 which is positioned laterally of porous tip 24b for expanding the lateral expanse of the apparatus for urging porous material 24b against the sidewall of the bore.

Figure 6:
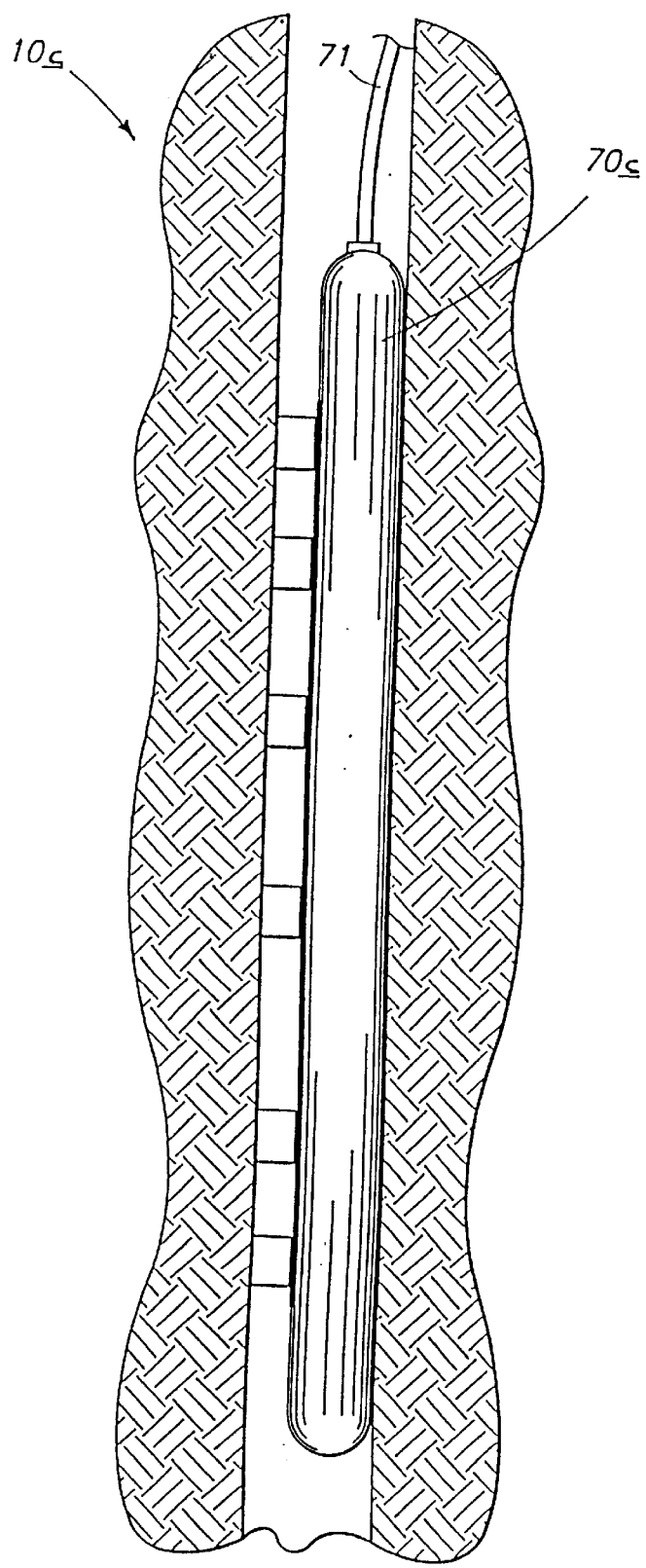
FIG. 6 is a longitudinal sectional view of another alternate embodiment sidewall tensiometer apparatus in accordance with the invention.

Another alternate embodiment 10c is diagrammatically shown in FIG. 6. Such diagrammatically comprises a plurality of sensors adhered to one side of a common inflatable bladder 70c at different elevations. This would enable moisture potential to be measured at different elevations within the soil. The sensors could be adhered to bladder 70c by velcro.

The above sidewall tensiometric measuring apparatus might of course also be constructed without an attached pressure sensing member, and instead use an accessible septum. For example, cap 62 (FIGS. 1 and 2) could comprise a septum.

Yet another alternate embodiment tensiometer apparatus 10d is illustrated in FIGS. 7 and 8. In this embodiment, a thin porous plastic sheet 24d is combined with a non-porous acrylic or PVC backing sheet 77. An example and preferred material for sheet 24d is wettable porous plastic (A-20 or A-40) manufactured by FMC. Backing sheet 77 is configured to provide a void 78 within the device, which is completely filled with a porous material 83. An example and preferred material is a plastic or fiberglass screen, or a scrim material. Sheets 24d and 78 are adhered to one another in fluid-tight communication via perimeter adhesive 79. A passageway 80 extends from the rear of non-pervious backing 77 to void 78, which is filled with screen 83. A PVC fitting 82 having opening 80 extending therethrough is provided against backing plate 77, and communicates with a conduit 84. Conduit 84 branches to fluid communicate with a transducer 30d, and a fill conduit 86.

Suitable bore sidewall engaging means such as an inflatable bladder would also be associated with the device, as described above. Such would be inflated once the device were inserted within a borehole to urge or push material 24d outwardly against the bore sidewall. The described materials are sufficiently flexible to enable the apparatus to curve or bend to conform to the general arcuate sidewall shape to provide intimate contact with the sidewall. Thus, this embodiment provides flexible, lateral sidewalls having porous material received therein which in this embodiment substantially fills the void, and is capable of flexibly conforming to the internal sidewalls surfaces.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A tensiometer to in situ determine below-grade soil moisture potential of earthen soil comprising:
   a body adapted for insertion into an opening in earthen soil below grade, the body having lateral sidewalls, the earthen opening having opposing lateral sides;
   a laterally oriented porous material provided relative to the body lateral sidewalls, the laterally oriented porous material at least in part defining a fluid chamber within the body;
   a pressure sensor in fluid communication with the fluid chamber; and
   sidewall engaging means for engaging a portion of a sidewall of an earthen opening to laterally urge the porous material into hydraulic communication with earthen soil of another portion of the earthen opening sidewall.

2. The tensiometer of claim 1 wherein the pressure sensor is mounted externally to the body.

3. The tensiometer of claim 1 wherein the sidewall engaging means comprises an inflatable bladder positioned laterally of the porous material.

4. The tensiometer of claim 1 wherein the sidewall engaging means comprises a piston and cylinder assembly positioned laterally of the porous material.

5. The tensiometer of claim 1 wherein the porous material has an arcuate periphery corresponding in male size and shape to a female arcuate periphery size and shape of a cylindrical earthen opening size for which the apparatus is adapted.

6. The tensiometer of claim 1 further comprising a flexible suspension support line operably connected to the body to lower and raise the tensiometer relative to an earthen opening.

7. The tensiometer of claim 1 further comprising a rigid support rod operably connected to the body to lower and raise the tensiometer relative to an earthen opening.

8. The tensiometer of claim 1 wherein the pressure sensor is mounted externally to the body, and the sidewall engaging means comprises an inflatable bladder positioned laterally of the porous material.

9. The tensiometer of claim 1 wherein the sidewall engaging means comprises an inflatable bladder positioned laterally of the porous material, and the porous material has an arcuate periphery corresponding in male size and shape to a female arcuate periphery size and shape of a cylindrical earthen opening size for which the apparatus is adapted.

10. The tensiometer of claim 1 wherein the sidewall engaging means comprises an inflatable bladder positioned laterally of the porous material, and further comprising a flexible suspension support line operably connected to the body to lower and raise the tensiometer relative to an earthen opening.

11. The tensiometer of claim 1 wherein the sidewall engaging means comprises an inflatable bladder positioned laterally of the porous material, and further comprising a rigid support rod operably connected to the body to lower and raise the tensiometer relative to an earthen opening.

12. The tensiometer of claim 1 wherein the porous material has an arcuate periphery corresponding in male size and shape to a female arcuate periphery size and shape of a cylindrical earthen opening size for which the apparatus is adapted, and further comprising a flexible suspension support line operably connected to the body to lower and raise the tensiometer relative to an earthen opening.

13. The tensiometer of claim 1 wherein the porous material has an arcuate periphery corresponding in male size and shape to a female arcuate periphery size and shape of a cylindrical earthen opening size for which the apparatus is adapted, and further comprising a rigid support rod operably connected to the body to lower and raise the tensiometer relative to an earthen opening.

14. The tensiometer of claim 1 wherein the body comprises a flexible lateral sidewall with the porous material being received therein.

15. The tensiometer of claim 1 wherein the body comprises a flexible lateral sidewall with the porous material being received therein, the porous material comprising a screen which substantially fills the fluid chamber.

16. The tensiometer of claim 1 comprising a plurality of said bodies with associated pressure sensors, the plurality of said bodies being elevationally spaced from one another along a common sidewall engaging means.

17. A tensiometer to in situ determine below-grade soil moisture potential of earthen soil comprising:
   A body having a lateral sidewall, wherein the body in operation is void of any mounted pressure sensing device, and the body comprises a normally closed pressure sensing device access port in fluid communication with the fluid chamber,
   A laterally oriented porous material provided along a substantial portion of the body lateral sidewall, the laterally oriented porous material at least in part defining a fluid chamber within the body.

18. The tensiometer of claim 17 comprising a plurality of said bodies, the plurality of said bodies being elevationally spaced from one another along a common inflatable bladder.

19. A method of monitoring soil moisture potential in below-grade earthen soil comprising the following steps:
   inserting a tensiometer into a below grade opening in earthen soil; the tensiometer having a porous material, a fluid chamber in fluid communication with the porous material, and a degassed liquid within the fluid chamber;
   laterally urging the porous material against a sidewall of the earthen opening to effectively establish hydraulic communication between the fluid chamber and the earthen material;
   permitting the degassed liquid to permeate the porous material to cause a change in pressure in the fluid chamber; and
   determining the change in pressure within the chamber.

* * * * *